US009873126B2

(12) United States Patent
Mao et al.

(10) Patent No.: US 9,873,126 B2
(45) Date of Patent: Jan. 23, 2018

(54) DEVICES AND METHODS FOR SEPARATING PARTICLES

(71) Applicant: University of Georgia Research Foundation, Inc., Athens, GA (US)

(72) Inventors: Leidong Mao, Athens, GA (US); Taotao Zhu, Athens, GA (US); Mark A. Eiteman, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 15/290,700

(22) Filed: Oct. 11, 2016

(65) Prior Publication Data

US 2017/0072405 A1   Mar. 16, 2017

Related U.S. Application Data

(62) Division of application No. 13/873,424, filed on Apr. 30, 2013, now Pat. No. 9,517,474.

(60) Provisional application No. 61/648,786, filed on May 18, 2012.

(51) Int. Cl.

| *B03C 1/32* | (2006.01) |
|---|---|
| *B03C 1/28* | (2006.01) |
| *G01N 27/74* | (2006.01) |
| *C12N 13/00* | (2006.01) |

(52) U.S. Cl.
CPC ............... *B03C 1/288* (2013.01); *B03C 1/32* (2013.01); *C12N 13/00* (2013.01); *G01N 27/74* (2013.01); *B03C 2201/18* (2013.01); *B03C 2201/26* (2013.01)

(58) Field of Classification Search
CPC ....... B03C 1/288; B03C 1/32; B03C 2201/18; B03C 2201/26; C12N 13/00; G01N 27/74
See application file for complete search history.

(56) References Cited

U.S. PATENT DOCUMENTS

| 4,756,884 A | 7/1988 | Hillman et al. |
|---|---|---|
| 5,957,298 A | 9/1999 | Buske et al. |
| 6,432,630 B1 | 8/2002 | Blankenstein |
| 6,482,328 B1 | 11/2002 | Davidson et al. |
| 6,994,219 B2 | 2/2006 | Roth et al. |
| 7,186,398 B2 | 3/2007 | Andres et al. |
| 7,364,921 B1 | 4/2008 | Sciorra et al. |
| 7,658,854 B2 | 2/2010 | Oder et al. |
| 8,083,069 B2 | 12/2011 | Murthy et al. |
| 2003/0159999 A1 | 8/2003 | Oakey et al. |
| 2007/0065808 A1 | 3/2007 | Bohm et al. |
| 2008/0178692 A1 | 7/2008 | Jung et al. |
| 2009/0014360 A1 | 1/2009 | Toner et al. |
| 2009/0050569 A1 | 2/2009 | Jung et al. |
| 2010/0297733 A1 | 11/2010 | Lin et al. |
| 2012/0055854 A1 | 3/2012 | Tibbe |

(Continued)

OTHER PUBLICATIONS

Forte, James Andrew, "Nonmagnetic particle separation using ferrofluids controlled by magnetic fields" (2009). Mechanical Engineering Master's Theses. Paper 21. http://hdl.handle.net/2047/d20000033.

(Continued)

*Primary Examiner* — David C Mellon
(74) *Attorney, Agent, or Firm* — Thomas | Horstemeyer, LLP

(57) ABSTRACT

Embodiments of the present disclosure provide for devices, methods for separating particles, and the like.

14 Claims, 8 Drawing Sheets

(56) References Cited

U.S. PATENT DOCUMENTS

2012/0080360 A1  4/2012  Stone et al.

OTHER PUBLICATIONS

Mao, Leidong, "A study of ferrohydrodynamics under traveling magnetic field excitations" (2008). Doctor of Philosophy Dissertation at Yale University. May 2008.

Zhu et al., Continuous separation of non-magnetic particles inside ferrofluids, Apr. 20, 2010, Springer-Verlag, Microfluid Nanofluid 9, pp. 1 003-1009.

Zhu et al., Continuous-flow ferrohydrodynamic sorting of particles and cells in microfluidic devices, Jun. 1, 2012, Springer-Verlag, Microfluid Nanofluid 13, pp. 645-654.

Kose et al., Ferrofluid mediated nanocytometry, Nov. 11, 2011, Royal Society of Chemistry, Lab Chip 12, pp. 190-196.

DEVICES AND METHODS FOR SEPARATING PARTICLES

CLAIM OF PRIORITY TO RELATED APPLICATION

This application is a divisional of U.S. patent application entitled "DEVICES AND METHODS FOR SEPARATING PARTICLES" having Ser. No. 13/873,424, filed on Apr. 30, 2013, which claims priority to U.S. provisional application entitled "DEVICES AND METHODS FOR SEPARATING PARTICLES" having Ser. No. 61/648,786, filed on May 18, 2012, the contents of which are incorporated herein by reference in their entirety.

STATEMENT REGARDING FEDERALLY SPONSORED RESEARCH OR DEVELOPMENT

This invention was made with Government support under Agreement No. 5 R21 GM104528-03, awarded by the National Institutes of Health. The Government has certain rights in the invention.

BACKGROUND

Microfluidic particle and cell sorting plays an important role in environmental monitoring, disease diagnostics, and therapeutics. Some techniques include labeling the particle or cell, however, these techniques have disadvantages. Thus, there is a need to develop alternative techniques for particle sorting.

SUMMARY

In accordance with the purpose(s) of the present disclosure, as embodied and broadly described herein, embodiments of the present disclosure, in one aspect, relate to a devices, methods for separating particles, and the like.

In an embodiment, a device, among others, includes: a first fluid inlet in a flow channel for flowing a first liquid including two or more types of particles, wherein the first liquid includes a magnetic fluid and/or is mixed with the magnetic fluid; a magnetic device configured to direct a non-uniform magnetic force onto the magnetic fluid and the particles; and a plurality of outlets, wherein the non-uniform magnetic force causes the types of particles to be separated and flow into different outlets.

In an embodiment, a method for separating particles, among others, includes: disposing at least two types of particles in a first fluid, wherein the first liquid includes and/or is mixed with the magnetic fluid; flowing the magnetic fluid and the particles down a channel; exposing the magnetic fluid and the particles to a non-uniform magnetic force; and separating the types of particles.

Other structures, compositions, methods, features, and advantages will be, or become, apparent to one with skill in the art upon examination of the following drawings and detailed description. It is intended that all such additional structures, systems, methods, features, and advantages be included within this description, be within the scope of the present disclosure, and be protected by the accompanying claims.

BRIEF DESCRIPTION OF THE DRAWINGS

Many aspects of this disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 2A-2C show the x-y plane (z=0), FIGS. 2D-2F illustrate the y-z plane (x=0), FIGS. 2G-2I illustrate the x-z plane (y=0) of magnetic field strength (surface plot) (FIGS. 2A, 2D, 2G), magnetic force (surface plot: force magnitude; arrow plot: force direction) (FIGS. 2B, 2E, 2I), and particles' trajectories (FIGS. 2C, 2F, 2I). Dots indicate starting points, while crosses indicate ending points of cells' trajectories. *E. coli* cell has volume range of 2.1-16.7 $\mu m^3$ and Yeast cell has volume range of 180-382 $\mu m^3$, resulting in a distribution of trajectories for each type of cell. The triangle in FIG. 2C indicates boundary between Outlets C and D. Dots indicate starting points, while crosses indicate ending points of cells' trajectories.

FIG. 3A, top and bottom, are photos showing *Escherichia coli* and Yeast colonies formed in M9 medium and EMG 408 ferrofluids after $10^6$ dilution from initial growth, respectively. FIG. 3B illustrates Colony Forming Unites (CFU) count of *Escherichia coli* and *Saccharomyces cerevisiae* using initial growth cell concentration.

FIGS. 4A, 4D, 4G illustrate particles/cells mixture (FIG. 4A: *Escherichia coli* (green) and 7.3 μm particles (red); FIG. 4D: *Saccharomyces cerevisiae* (red and bright-field) and 1.0 μm particles (green); FIG. 4G: *Escherichia coli* (green) and *Saccharomyces cerevisiae* (red and bright-field) before magnetic fields were applied. FIGS. 4B, 4E, 4H illustrate micrographs of Outlet C after magnetic fields were applied, and FIGS. 4C, 4F, 4I were micrographs of Outlet D. Blue triangles indicate boundary between Outlets C and D. Scale bars represent 200 μm.

FIGS. 5A-5D illustrate *Escherichia coli* and 7.3 μm particles mixture; FIGS. 5E-5H illustrate *Saccharomyces cerevisiae* and 1.0 μm particles mixture; FIGS. 5I-5L illustrate *Escherichia coli* and *Saccharomyces cerevisiae* mixtures. The bar with normal number on top shows remaining efficiency, while the bar with italic number on top shows separation efficiency. Scale bars represent 200 μm.

FIGS. 8A-8D illustrate HeLa cell and red blood cells in channel before magnetic fields were applied. FIGS. 8E-8J were micrographs after magnetic fields were applied. FIGS. 8H-8J illustrate micrographs of Outlet 1-6. Scale bars represent 200 µm.

FIGS. 11A-11D were superimposed micrographs of 15.5 µm and 5.8 µm particles mixture. FIGS. 11E-11H illustrates HeLa cell and 5.8 µm particles mixture. FIGS. 11A-11B, 11E, and 11F illustrates micrographs of inlets and outlets before magnetic fields were applied. FIGS. 11C, 11D, 11G, 11H illustrate micrographs of inlets and outlets after magnetic fields were applied. Scale bars represent 200 µm.

DISCUSSION

Figures 1A, 1B, 1C, 1D:
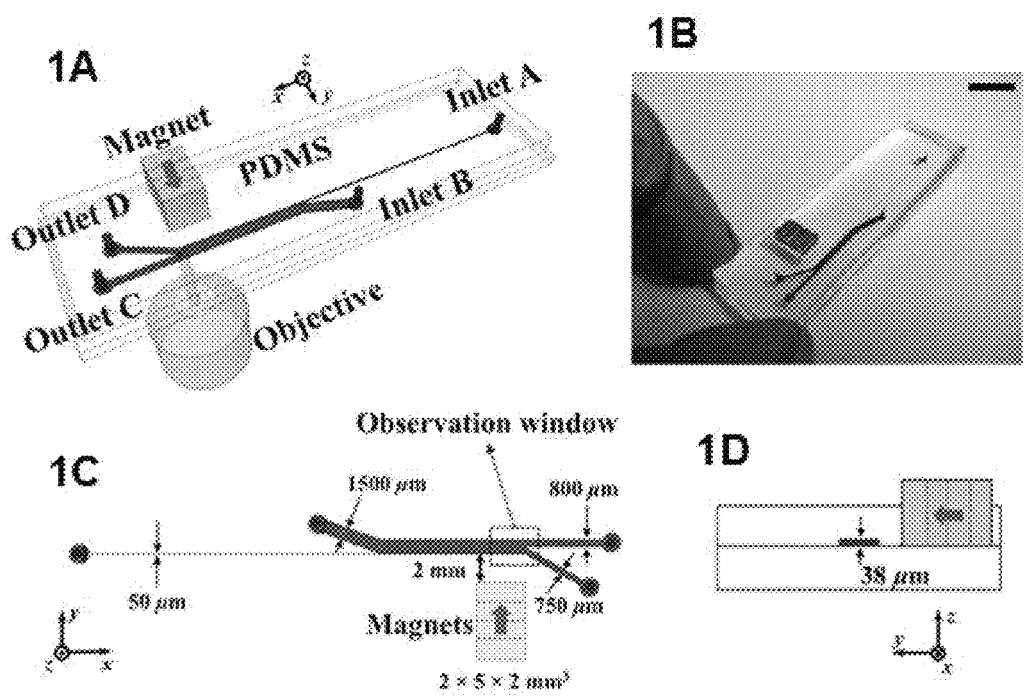
FIG. 1A illustrates a schematic representation of the sorting device with permanent magnets and a microfluidic channel.
FIG. 1B illustrates an image of protype device. Scale bar is 10 mm.
FIG. 1C illustrates a topview of the device and relevant dimensions. The arrows indicate direction of magnets' magnetization.
FIG. 1D illustrates a cross-section of the device.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed. Terms defined in references that are incorporated by reference do not alter definitions of terms defined in the present disclosure or should such terms be used to define terms in the present disclosure they should only be used in a manner that is inconsistent with the present disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, material science, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmosphere. Standard temperature and pressure are defined as 25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Discussion

Embodiments of the present disclosure provide for devices, methods for separating particles, and the like. An embodiment of the present disclosure is advantageous because it has a very high sorting efficiency (e.g., about 95% or more, about 99% or more, about 99.9% or more) and a very high throughput (e.g., about $10^7$ cells/hour or more, about $10^8$ cells/hour or more). In addition, the device is less expensive than other techniques (e.g., FACS) and is straightforward to operate.

In general, embodiments of the present disclosure include non-uniform magnetic field-assisted processes and devices for the separation of particles (e.g., cells) within a magnetic fluid. Under non-uniform magnetic fields, particles such as cells can experience the generated magnetic field direction to produce a magnetic buoyancy force, analogous to buoyancy force, as magnitude of the force is proportional to the volume of cell. This force can be used to spatially separate cells of different sizes in certain flow conditions (e.g., laminar flow). Embodiments of the present disclosure can be label-free and/or do not require time-consuming steps of magnetic beads conjugation. Embodiments of the present disclosure include high-efficiency and high-throughput continuous-flow particle separation and focusing devices using magnetic fluid (e.g., ferrofluids) and magnets (e.g., permanent magnets). Permanent magnet based devices are low-cost and easy to operate and their operations does not generate heat. Magnetic fields produced by permanent magnets are substantially larger than the ones by current-carrying electrodes, which can increase the sorting throughput and efficiency of embodiments of the present disclosure.

In an exemplary embodiment, the device includes a first fluid inlet in a flow channel for flowing a first liquid including two or more types of particles, where the first liquid includes a magnetic fluid. In an embodiment, additional inlets can be present to introduce other reagents or fluids. For example, the cells can be flowed in the first fluid inlet and the magnetic fluid can be flowed in a second fluid inlet, where the two fluids mix in or prior to introduction to the channel. In an embodiment, the flow rate of the fluid(s) can be controlled and the flow rate can be used to enhance the separation.

In an embodiment the channel can have a constant diameter along its length. In another embodiment, the channel can have a tapered diameter. In an embodiment, the flow chamber can be designed to optimize the separation of the particles.

In an embodiment, the channel can have a length of about 5000 µm to 20000 µm prior to splitting into two or more outlets (e.g., 2 to 100), and a diameter of about 1000 to 2000 µm. In an embodiment, the outlets (e.g., outlet channels) can have the same or different diameters and can independently have a diameter of about 500 to 2000 µm. In an embodiment, the outlets can be designed (e.g., diameter, three-dimensional orientation relative to the channel (e.g., offset from the axis of the channel), and the like) to enhance the separation of the particles.

In an exemplary embodiment of the device, a magnetic device configured to direct a non-uniform magnetic force onto particles is positioned at a point of the channel. In an embodiment, the magnetic device can be positioned relative to the split from the channel to the outlets. In an embodiment, the magnetic device is configured to direct the non-uniform magnetic force onto particles from one side of the channel. As noted above, the design of the device (e.g., the position of the magnetic device and/or the outlets) can take into consideration the various components, the particles to be separated, and/or the magnetic fluid, to achieve the desired separation efficiency and/or throughput.

In an embodiment, the magnetic energy can be produced using a magnetic device that includes one or more permanent magnets positioned to produce a non-uniform magnetic field in at least a portion of the channel. In an embodiment, one permanent magnet is disposed on one side of the channel to generate the non-uniform magnetic force. The strength of the magnetic field can be selected based upon the configuration of the device, the particles to be separated (e.g., the volume of the particles), and the like. In another embodiment, the magnetic device includes three or more magnets (e.g., 3, 4, 5, 6, 7, and so on) that can be used to form a non-uniform magnetic field within an area of the channel. The design, number of magnets used, the non-uniform magnetic field generated, and the like, can be designed to separate particles.

As noted above, the device includes a plurality of outlets. Once the non-uniform magnetic force acts upon the particles, the particles flow in the first fluid is altered so that certain types of particles flow into one outlet and another type of particle flows into a different outlet.

In an embodiment where many different types of particles are to be separated, then the outlets can be spaced apart along the length of the channel and/or more than one magnet can be used along the length of the channel in conjunction with the spacing of the outlet. Many different types of configurations are envisioned that are consistent with the teachings of the present disclosure and are intended to be covered by claims of this and future application.

In an embodiment, the particles can experience non-uniform magnetic force and are biologically compatible with the magnetic fluid. In particular, the particles can be separated by the magnetic buoyancy force exerted upon them. In an embodiment, the particles can include cells, polystyrene microparticles, and a combination thereof. In an embodiment, the cells can include bacterial cells, yeast cells, blood cells, cancer cells, neural cells, sperm cells, eggs, as well as types of cells that have size difference can be distinguished by this technique. In an embodiment, the cells can include *Escherichia coli, Saccharomyces cerevisiae, Lactobacillus casei*, red blood cells, Jurkat cells, and HeLa cells. In an embodiment, the volume of the cells can be about 5 to 3000 µm$^3$.

In an embodiment, the particles are mixed with a magnetic fluid (e.g., prior to introduction to the device and/or within the device). In an embodiment, the magnetic fluid is a colloidal mixture of nano-size magnetic particles (e.g., about 5 to 10 nm in diameter), covered by a surfactant, suspended in a compatible carrier medium. In an embodiment, the magnetic particles can be iron oxide particles, cobalt particles, cobalt ferrite particles, iron particles, and FePt particles, or a combination thereof, where the amount of the magnetic particles in the magnetic fluid can be about 1% (v/v) to 10% (v/v). In an embodiment, the surfactant can include electric double layer surfactant, polymer surfactant, inorganic surfactant, or a combination thereof. In an embodiment, the carrier medium can include water, hydrocarbon oil, kerosene, or a combination there. In an embodiment, the magnetic fluid can be a ferrofluid, paramagnetic solution, or a combination thereof.

As mentioned above, embodiments of the present disclosure include a method for separating particles, where the device described herein can be used to perform steps of the method. In an embodiment, the method is a continuous flow method. In an embodiment, the at least two types of particles are disposed in fluid including a magnetic fluid (e.g., a first fluid). In an embodiment, the fluid including the particles and the magnetic fluid are flowed down the channel. At a position in the channel (e.g., a first area), the fluid is exposed to a non-uniform magnetic force, where a magnetic device can be used to generate the non-uniform magnetic force. In an embodiment, the particles experience a magnetic buoyancy force that causes the particles to separate from one another based on the volume of the particles. In an embodiment, the particles can be separated from one another into two or more outlets.

In an embodiment, this process can be repeated for the particles that are separated to increase efficiency and/or separate particles having similar characteristics (e.g., volume). For example, the separated flow can be recirculated through the same channel or can be flowed through a different channel is a device include two or more channels and magnets.

EXAMPLES

Now having described the embodiments of the disclosure, in general, the example describes some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Brief Introduction:

A new sorting scheme based on ferrofluid hydrodynamics (ferrohydrodynamics) was used to separate mixtures of particles and live cells simultaneously. Two species of cells, including *Escherichia coli* and *Saccharomyces cerevisiae*, as well as fluorescent polystyrene microparticles were studied for their sorting throughput and efficiency using a commercial ionic ferrofluid. To separate mammalian cells including blood cells, cervical cancerous cells and epithelial cells, a lab-customized ferrofluid was used. Ferrofluids are stable magnetic nanoparticles suspensions. Under external magnetic fields, magnetic buoyancy forces exerted on particles and cells lead to size-dependent deflections from their laminar flow paths and result in spatial separation. We report the design, modeling, fabrication and characterization of the sorting devices. This scheme is simple, low-cost and label-free compared to other existing techniques.

Introduction:

Microfluidic particle and cell sorting plays an important role in environmental monitoring (Liu et al. 2004; Beyor et al. 2008; Dharmasiri et al. 2010), disease diagnostics (Nagrath et al. 2007; Adams et al. 2008; Hoshino et al. 2011), and therapeutics (Toner and Irimia 2005; Yung et al. 2009). Compared to high-specificity and label-based cell sorting techniques such as fluorescence-activated cell sorter (FACS) (Bonner et al. 1972) and magnetic-activated cell sorter (MACS) (Miltenyi et al. 1990), microfluidic sorting is mostly label-free, relying on cells' intrinsic properties such as size, shape, density, deformability, electric and magnetic properties for manipulation specificity (Pamme 2007; Tsutsui and Ho 2009; Gossett et al. 2010; Lenshof and Laurell 2010). When applicable, microfluidic sorting is favored over label-based ones, because they are inexpensive and require minimal user training for operation (Gossett et al. 2010). Among them, those based on channel design including pinched flow fractionation (Yamada et al. 2004) and deterministic lateral displacement (Huang et al. 2004; Davis et al. 2006) combine laminar flows with mechanical structures to direct particles of different sizes into separate streamlines. Continuous inertial separation uses balance between inertial lift force and Dean drag force in curved channels for size-dependent sorting of particles and cells (Di Carlo 2009). On the other hand, external energy inputs such as acoustic, electric and magnetic forces have also been used to manipulate cells in microfluidic systems. Depending on the application, their simpler channel geometry and faster manipulation speed may outweigh the complications of integrating electrodes in their designs. For example, acoustophoresis can separate particles and cells according to their size, density, as well as compressibility (Laurell et al. 2007; Shi et al. 2009; Wang and Zhe 2011). Dielectrophoresis (DEP), arising from interactions of cells' dipoles and their surrounding electric fields, can realize low-cost and integrated devices for cell manipulation (Voldman 2006).

Magnetophoresis (MAP) takes advantages of paramagnetic nature of red blood cells and magnetotactic bacteria and applies non-uniform magnetic fields to separate them from non-magnetic objects (Zborowski et al. 2003; Lee et al. 2004). However, most applications of magnetophoresis use functionalized magnetic beads for labeling (Pamme 2006; Liu et al. 2009; Gijs et al. 2010). The label-based methods are manually intensive and time-consuming. The magnetic moments of these beads, even from the same batch, can vary dramatically due to their manufacturing procedure, making scaling of the method scaling difficult (Hafeli et al. 1997; Miller et al. 2001; Rife et al. 2003; Mihajlovic et al. 2007; Shevkoplyas et al. 2007).

To address problems with label-based magnetophoresis, a label-free technique that uses reverse magnetophoresis to manipulate and sort cells has been developed recently based on ferrofluid hydrodynamics (ferrohydrodynamics) (Yellen et al. 2005; Kose et al. 2009; Zhu et al. 2010; Zhu et al. 2011a; Kose and Koser 2012). Ferrofluids are colloidal suspensions of magnetic nanoparticles, typically magnetite ($Fe_3O_4$) with approximately 10 nm diameters (Rosensweig 1985). They are covered by either electrostatic or steric surfactants to keep them from agglomeration due to van der Waals force and in suspension within a water or oil medium. Ferrohydrodynamics studies mechanics of ferrofluid motion under external magnetic fields (Rosensweig 1985; Odenbach and Editor 2002). Its applications in microfluidics, recently reviewed by Nguyen (Nguyen 2012), include miniaturized polymerase chain reaction (PCR) (Sun et al. 2007; Sun et al. 2008), traveling-wave magnetic field pumping (Mao and Koser 2006; Mao et al. 2011), micro-scale mixing (Mao and Koser 2007), micropump (Hatch et al. 2001; Love et al. 2004), and droplet manipulation (Nguyen et al. 2006; Zhang et al. 2011b, a).

In applications of cell manipulation, the purpose of using ferrofluids is to induce effective magnetic dipole moments within cells. Under non-uniform magnetic fields, cells will experience in the weaker field direction a magnetic buoyancy force, analogous to buoyancy force, as magnitude of the force is proportional to the volume of cell (Rosensweig 1985). Many groups have been working on adapting this principle to particles and cells sorting. For example, Whitesides' group separated synthetic particles according to their densities' difference using paramagnetic salt solutions (Winkleman et al. 2007; Mirica et al. 2009). Pamme's group demonstrated continuous particle and cell manipulation using paramagnetic salt solution in microfluidic devices (Peyman et al. 2009; Rodriguez-Villarreal et al. 2011). Xuan's group studied the transport of particles in both paramagnetic solutions and ferrofluids through a rectangular microchannel embedded with permanent magnets (Liang et al. 2011; Zhu et al. 2012). Park's group recently sorted human histolytic lymphoma monocytes cells from red blood cells using gadolinium diethylenetriamine pentaacetic acid (Gd-DTPA) solution (Shen et al. 2012). However, magnetic susceptibility of paramagnetic salt solutions is inherently small, about 5 orders of magnitude weaker than that of a ferrofluid (Krebs Melissa et al. 2009), rendering slower manipulation speed and low throughput. As a result of the higher susceptibility of ferrofluids, Koser's group was able to use an integrated microfluidic platform for sorting of microparticles and live cells within a citrate stabilized cobalt-ferrite ferrofluid in static flow conditions (Kose et al. 2009). The same device was also applied to continuous-flow frequency-adjustable particles separation (Kose and Koser 2012). Our group developed high-efficiency and high-throughput continuous-flow particle separation and focusing devices using commercial ferrofluids and hand-held permanent magnets (Zhu et al. 2010; Zhu et al. 2011b; Zhu et al. 2011a). Permanent magnet based devices are low-cost and easy to operate; their operations do not generate heat. Magnetic fields produced by permanent magnets are substantially larger than the ones by current-carrying electrodes.

High throughput, label-free and selective cell sorting realized in a single automated device can have profound impacts on environmental monitoring, diagnostics and therapeutics. Although continuous-flow ferrohydrodynamic sorting has been demonstrated with microparticles, it has not previously been reported with live cells (Zhu et al. 2010). The potential for live cell applications of continuous-flow ferrohydrodynamic sorting motivates the study presented here. We developed a microfluidic device that could continuously sort cells of different sizes based on ferrohydrodynamics, which involved manipulation of cells within ferrofluids via external non-uniform magnetic fields. When cell mixtures and ferrofluids were injected into the channel by a pressure-driven flow, deflections of cells from their laminar flow paths would occur because of the magnetic field gradient and resulting magnetic buoyance force. This deflection will lead to spatial separation of cells of different sizes at the end of channel.

In the following sections, we first summarize materials and methods used in this study, followed by results from a three-dimensional theoretical study of cells' transport in the microfluidic device. In the first embodiment, cell viabilities of *Escherichia coli* and *Saccharomyces cerevisiae* in a commercial ferrofluid are discussed. Afterwards, calibration of the sorting device with fluorescent polystyrene microparticles is performed. *Escherichia coli* and *Saccharomyces cerevisiae* are sorted in the device, and cells distribution is analyzed on samples collected from channel outlets. In the second embodiment, cell viabilities of red blood cells, HeLa cells, in the customized ferrofluid are tested. A stronger magnetic field gradient is applied to enable particles focusing. Calibration of the sorting device with polystyrene microparticles of comparable size is performed before sorting the cells. Cell distribution is analyzed on samples collected from six channel outlets. In the third embodiment, a new one-step separation micro-device without the need of washing cells after enrichment was developed. This device takes in cells sample in its natural reagent or ferrofluids, separate them based on their sizes, and return purified cells to an outlet. It eliminates the preparation and washing steps typically associated with our device. In the end we will discuss outlook of ferrohydrodynamic sorting.

Figures 6A, 6B, 6C, 6D:
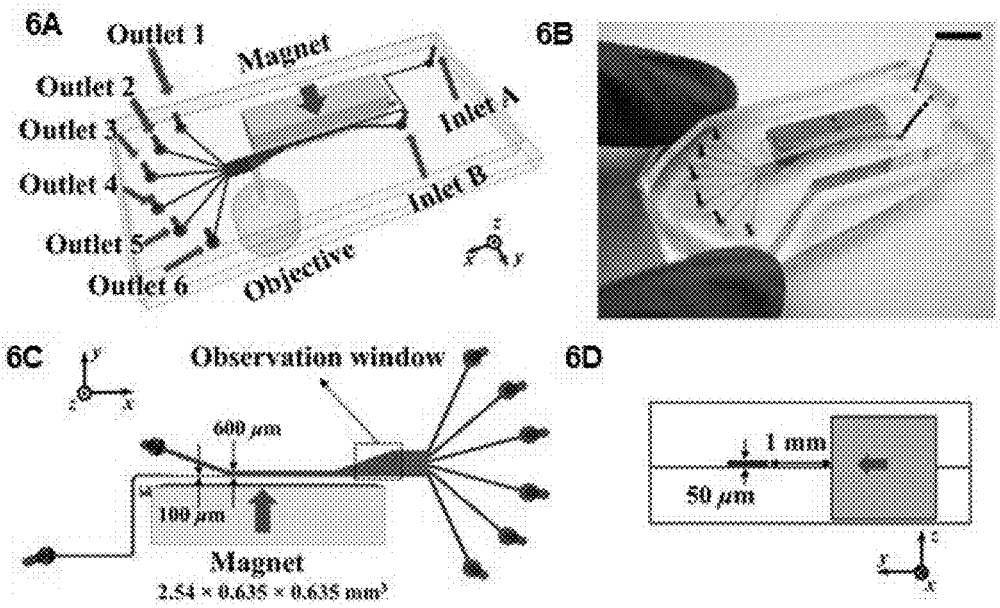
FIG. 6A illustrates a schematic representation of the sorting device with permanent magnets and a microfluidic channel.
FIG. 6B illustrates an image of protype device. Scale bar is 10 mm.
FIG. 6C illustrates a topview of the device and relevant dimensions. The arrows indicate direction of magnets' magnetization.
FIG. 6D illustrates a cross-section of the device.

Materials and Methods:

The prototype polydimethylsiloxane (PDMS) microfluidic device was fabricated through a standard soft-lithography approach and attached to a flat surface of another piece of PDMS, as shown in FIGS. 1A-1B. A mask of the device pattern was created using AutoCAD 2008 (Autodesk Inc., San Rafael, Calif.) and printed by a commercial photoplotting company (CAD/Art Services Inc, Bandon, Oreg.). In the first embodiment, dimensions of the microfluidic channel are listed in FIGS. 1C-1D. Thickness of the device was measured to be 38 µm by a profilometer (Dektak 150, Veeco Instruments Inc., Chadds Ford, Pa.). Before attachment, PDMS surfaces were treated with plasma (PDC-32G plasma cleaner, Harrick Plasma, Ithaca, N.Y.) at 11.2 Pa $O_2$ partial pressure with 18 W power for 1 minute. A stack of four NdFeB permanent magnets was embedded into PDMS channel with their magnetization direction vertical to the channel during curing stage. Each magnet is 5 mm in width, 5 mm in length and 2 mm in thickness. The magnet stack was placed 2 mm away from the channel. Flux density at the center of magnets stack's surface was measured to be 470 mT by a Gauss meter (Model 5080, Sypris, Orlando, Fla.) and an axial probe with 0.381 mm diameter of circular active area. In the second embodiment, dimensions of the microfluidic channel are listed in FIGS. 6C-6D. Thickness of the device was measured to be 50 µm by a profilometer (Dektak 150, Veeco Instruments Inc., Chadds Ford, Pa.). A NdFeB permanent magnets was embedded into PDMS channel with their magnetization direction vertical to the channel during curing stage. The magnet is 2.54 cm in width, 6.35 mm in length and thickness. The magnet stack was placed 1 mm away from the channel. Flux density at the center of magnets stack's surface was measured to be 470 mT. In the third embodiment, dimensions of the microfluidic channel are listed in FIGS. 10C-10D. Thickness of the device was measured to be 50 µm by a profilometer (Dektak 150, Veeco Instruments Inc., Chadds Ford, Pa.). A NdFeB permanent magnets was embedded into PDMS channel with their magnetization direction vertical to the channel during curing stage. The magnet is 2.54 cm in width, 3.175 mm in length and thickness. The magnet stack was placed 2 mm away from the channel. Flux density at the center of magnets stack's surface was measured to be 470 mT. Before liquid injection, the device was treated with plasma for 10 minutes to render PDMS surfaces hydrophilic. This step ensured both cells and microparticles would not attach onto PDMS surfaces during sorting.

In the first embodiment, we used a commercial water-based, pH ~7 magnetite ferrofluid coated with anionic surfactants (EMG 408, Ferrotec Co., NH). Volume fraction of magnetite particles in this ferrofluid is 1.1%. Mean diameter of nanoparticles has been determined from Transmission Electron Microscopy (TEM) images to be ~10 nm. Initial magnetic susceptibility was measured to be 0.26; saturation magnetization was 60 Gauss; viscosity was $1.2 \times 10^{-3}$ kg/m·s. *Escherichia coli* (strain MG1655) and *Saccharomyces cerevisiae* (Baker's yeast), and two fluorescent microparticles (green 1.0 µm diameter, Thermo Fisher Scientific Inc., Waltham, Mass., and red 7.3 µm diameter, Bangs Laboratories Inc., Fishers, Ind.) were used in sorting. In the second and third embodiment, we used a water-based, pH ~7 maghemite ferrofluid coated with polyethylene glycol copolymer (ATLOX4913, Croda. Inc). Volume fraction of magnetite particles in this ferrofluid is 1%. Mean diameter of nanoparticles has been determined from Transmission Electron Microscopy (TEM) images to be ~5.13 nm. Initial magnetic susceptibility was measured to be 0.098; saturation magnetization was 2.93 kA/m.

Ferrofluid and particles/cells mixture injected into microchannel were maintained at tunable flow rates using a syringe pump (Nexus 3000, Chemyx Inc., Stafford, Tex.). Sorting was conducted on the stage of an inverted microscope (Zeiss Axio Observer, Carl Zeiss Inc., Germany). Micrographs of cells and particles were recorded through either a green fluorescent filter set (41001 FITC, Chroma Technology Corp., Rockingham, Vt.), or a red filter set (43HE, Carl Zeiss Inc., Germany), and a CCD camera (SPOT RT3, Diagnostic Instruments, Inc., Sterling Heights, Mich.). Cell samples collected from channel outlets were pipetted onto microscope slides and analyzed using a highresolution CCD camera (AxioCam HR, Carl Zeiss Inc., Germany) for size distributions to quantitatively evaluate efficiency of this approach. ImageJ® software was used to count the number of cells.

Saccharomyces cerevisiae (Baker's yeast) cells were first grown in a 10 ml test tube containing 2 ml of YPG medium (10 g/l yeast extract, 20 g/l glucose, 20 g/l glucose) overnight. They were then transferred into a 100 ml shake flask containing 20 ml of YPG medium. After 4 h growth at 30° C. and 250 rpm, cells in the flask were stained with fluorophores. Escherichia coli (strain MG1655) cells were first grown in a 10 ml test tube containing 2 ml of Luria-Bertani (LB) medium overnight. They were then transferred into a 100 ml shake flask containing 20 ml of LB medium (25 g/l LB). After 4 h growth at 37° C. and 250 rpm, cells were stained with fluorophores. Nucleic acid stains SYTO9 (green) and SYTO17 (red) (Molecular Probes Inc., Eugene, Oreg.) were used in cell staining.

Hela cells were cultured in culture flasks (BD Falcon) containing 12 mL of DMEM medium with 10% (v/v) fetal bovine serum, 100 U/mL penicillin, and 100 µg/mL streptomycin. All cell lines were incubated (5% $CO_2$, 90% humidified) at 37° C. in an incubator (Innova-Co 170; New Brunswick Scientific, U.K.) prior to use. Cells were subcultured at a ratio of 1:5 every 3 days to maintain cells in the exponential growth phase. Cells were detached from the flask with the treatment of 0.25% (w/v) trypsin-EDTA solution (Gibco) for 3 min for harvest. Cells were then suspended in the culture media at a concentration of $2\times10^6$ cells/mL before use.

To study of viability of Escherichia coli and Saccharomyces cerevisiae cells exposed to EMG 408 ferrofluids, nominally $2\times10^9$ cells Escherichia coli and $2\times10^7$ cells Saccharomyces cerevisiae grown as described above were centrifuged twice at 4° C. and washed in defined M9 medium (6.78 g/l $Na_2HPO_4$, 3.0 g/l $KH_2PO_4$, 0.5 g/l NaCl, 1.0 g/l $NH_4Cl$) without carbon source. For either cell type in duplicate, the washed cell pellet from centrifugation was combined with either 2 ml of EMG 408 ferrofluid or 2 ml M9 medium as a control. After 2 hours of incubation at room temperature in these fluids, cell density was determined in triplicate using standard microbial serial dilutions ($10^6$ dilution for Escherichia coli, and $10^4$ dilution for Saccharomyces cerevisiae), with the transferring of known volumes to Petri plates and counting of Colony Forming Units (CFU) after 24 hours.

To study the viability of HeLa, red blood cells exposed to PEG-ferrofluids, nominally $2\times10^6$ cells grown as described above were centrifuged twice at 4° C. and washed in Hank's buffer solution (HBSS). For either cell type in duplicate, the washed cell pellet from centrifugation was combined with either 1 ml of PEG ferrofluid or 1 ml HBSS as a control. After 2 hours of incubation at room temperature in these fluids, cell viability was determined with trypan blue staining and counted with a haemocytometer.

Theory and Simulation:

Previously, we reported both two-dimensional (2D) and three-dimensional (3D) analytical models for microfluidic transports of microparticles in ferrofluids (Zhu et al. 2011a; Zhu et al. 2011b). In this work, we applied the 3D analytical model to predict cells' sorting in permanent magnet based device. Briefly, we obtained cells' trajectories by first calculating magnetic buoyancy force on cells using a 3D analytical model of magnetic fields (Furlani and Sahoo 2006) and a nonlinear magnetization model of ferrofluids (Rosensweig 1985), and then solving governing equations of motion for cells in laminar flow condition (Brody et al. 1996). All relevant parameters used in our simulation are listed in FIGS. 1A-1D and Materials and Methods section. In addition, we calculated volume of a single rod-shape Escherichia coli cell with short axis of 0.5-1 µm and long axis of 2-4 µm to be 2.1-16.7 $\mu m^3$ (Kaya and Koser 2009), and volume of a single sphere-shape Saccharomyces cerevisiae cell with diameter of 7-9 µm to be 180-382 $\mu m^3$ (Jorgensen et al. 2002).

Figures 2A, 2B, 2C, 2D, 2E, 2F, 2G, 2H, 2I:
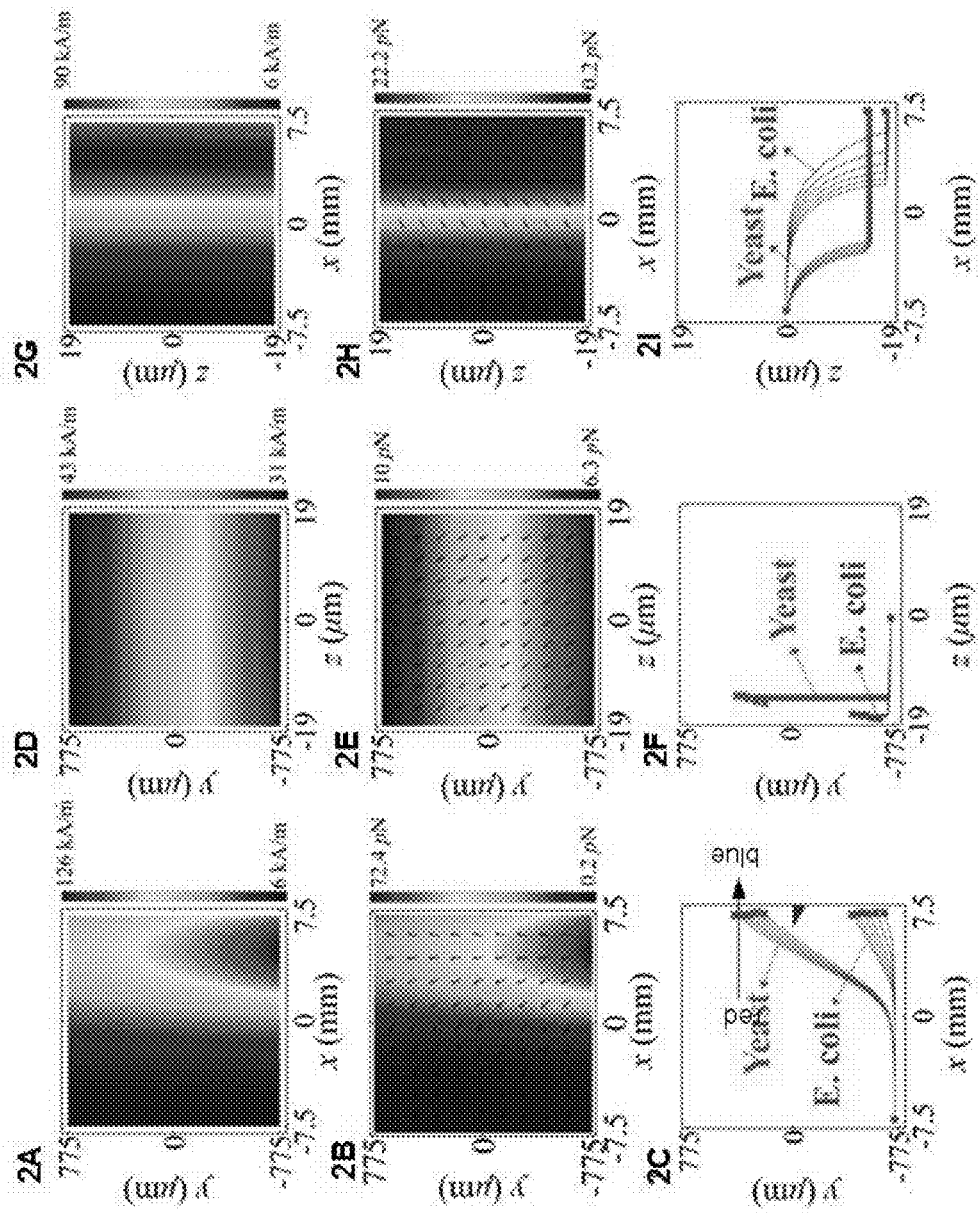
FIGS. 2A-2I illustrate an analytical three-dimensional simulation of magnetic field and force distributions in microfluidic channel, and trajectories of cells. Simulation parameters match exact experimental conditions.

FIGS. 2A-2I summarize simulated distribution of magnetic fields and magnetic buoyance forces in the sorting channel, as well as 3D trajectories of Escherichia coli and Saccharomyces cerevisiae cells. The surface plot in FIG. 2A shows magnitude of magnetic fields of x-y plane at z=0. Magnetic fields decayed rather quickly from the surface of the magnet and formed a gradient that resulted in magnetic buoyance force on cells in both x and y directions, as indicated in FIG. 2B. Consequently, cells experiencing such force when entering the sorting channel would decelerate in x direction and accelerate in y direction. Force computed on a spherical microparticle of 7.3 µm diameter, with its total volume (~200 $\mu m^3$) close to that of a single Saccharomyces cerevisiae cell, is on the order of 10 pN. Cell mixtures were quickly sorted by magnetic buoyancy force towards the end of channel, as shown in FIG. 2C with simulated cells' trajectories considering their natural size variations. All Escherichia coli cells, having much smaller size and volume compared to Saccharomyces cerevisiae cells, exited the channel through Outlet D, while all Saccharomyces cerevisiae cells migrated towards Outlet C. FIGS. 2D-2F illustrate distribution of magnetic fields and forces, as well as trajectories of cells of y-z plane at x=0; FIGS. 2G-2I depict the cases of x-z plane at y=0. We are interested in 3D trajectories of cells, in part due to the opaqueness of ferrofluids and difficulty in recording cells' weak fluorescence in the channel, especially the red fluorescent from Saccharomyces cerevisiae cells, as shown later in the results. In a concentrated ferrofluid (~10% v/v), particles and cells are visible only when they are very close (~1 µm) to the surface of channel (Zhu et al. 2011b). Visibility was a less of a problem when diluted ferrofluids (~1% v/v) and thin microchannel were used in our device. Simulation results from FIGS. 2F-2I indicated in our current setup all cells were pushed towards the channel bottom surface, which would enhance visibility of stained cells.

Results and Discussions:

Cell Viability

Figures 3A, 3B:
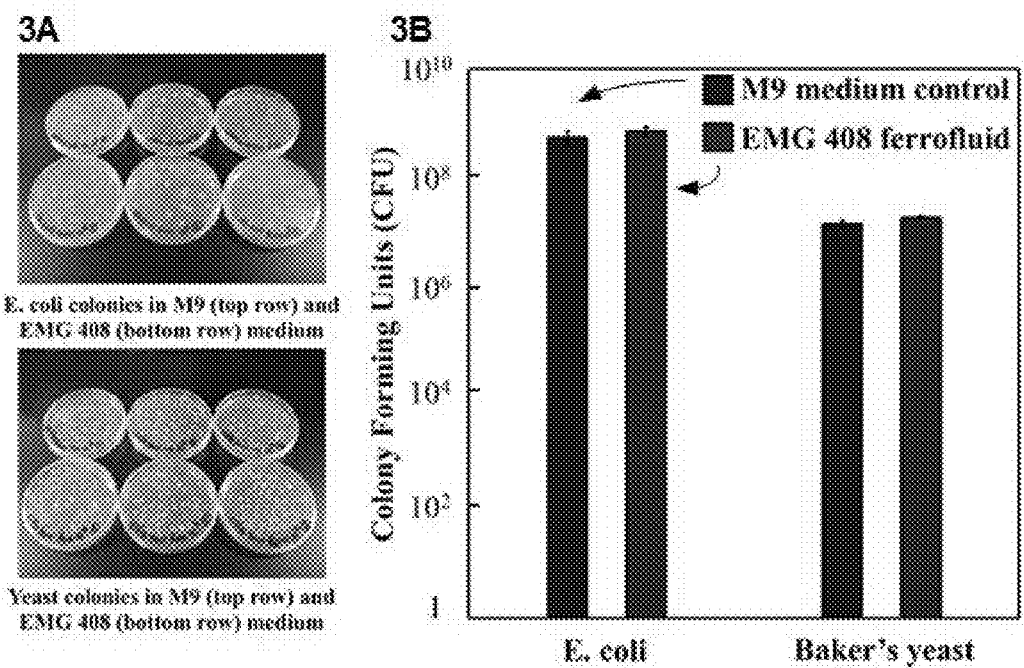
FIGS. 3A-3B illustrate cell viability test of *Escherichia coli* and *Saccharomyces cerevisiae*.

FIG. 3A shows the CFU in both M9 medium and EMG 408 ferrofluids after incubation. Counts of CFU for each case were averaged over 3 plates and plotted in FIG. 3B. We observed a slight increase in cell density after 2 hours of incubation in the ferrofluid compared to the M9 medium control for both cell types, suggesting a possibility that either the EMG 408 ferrofluid acted as a cell protectant or the cells continued to grow in this ferrofluid during incubation. Nonetheless, this ferrofluid was not detrimental to the viability of both cell types after 2 hours of exposure, which allowed enough time to carry out the sorting procedure.

Figure 7:
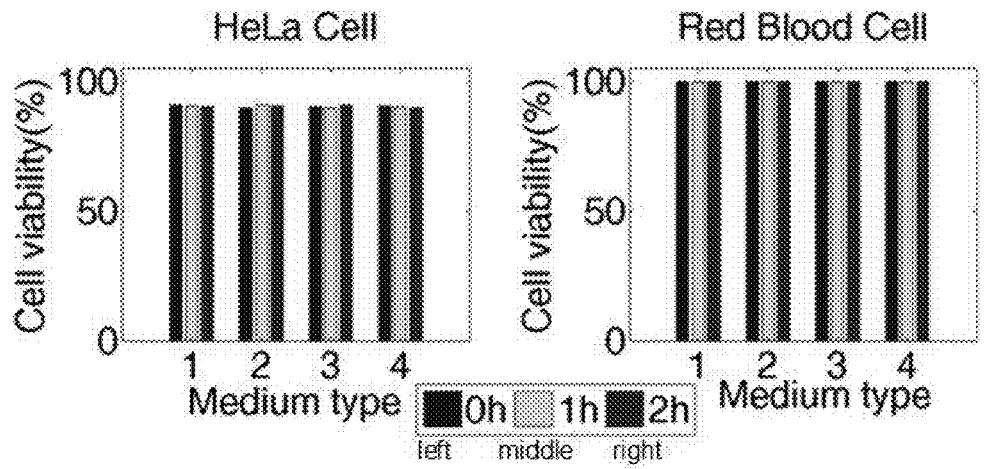
FIG. 7 illustrates cell viability test of HeLa cell and red blood cell in Hank's Balanced Salt Solution (HBSS) and PEG ferrofluids, medium 1 is HBSS, medium 2 to 4 are PEG ferrofluid with magnetic nanoparticles volume fraction of 0.395%, 0.79%, 1% respectively. After 0, 1, and 2 hours incubation, HeLa cell and red blood cell viability are counted with trypan blue dye exclusion assay.

FIG. 7 shows the viability of HeLa cells and mouse red blood cells in both HBSS and PEG ferrofluids after incubation. We counted the cell numbers with trypan blue viability staining after 2 hours of incubation in the ferrofluid compared with the HBSS control for both cell types, Cells Sorting:

In the first embodiment, we first calibrated the sorting device using a mixture of Escherichia coli cells and red fluorescent 7.3 µm particles, which have similar total volume of Saccharomyces cerevisiae cells. Washed Escherichia

*coli* cell pellet from centrifugation as described above was stained with 1 μl of green nucleic acid stain SYTO9. Both particles and cells have concentrations of ~$10^7$ counts/ml. We introduced microparticles/cells mixture into microfluidic channel Inlet A at a constant flow rate of 1.5 μl/min. The mixture was hydrodynamically focused into a narrow stream by sheath flow from Inlet B at a flow rate of 6 μl/min. The observation window was located right before the channel outlets, as indicated in FIG. 1C. When magnetic fields were off, particles and cells were observed in fluorescent mode flowing together near sidewall of the channel and exiting through Outlet D, as shown in composite micrograph of FIG. 4A. When magnetic fields were on, magnetic buoyancy forces deflected particles from their laminar flow paths towards Outlet C, as shown in FIG. 2B. On the other hand, forces on smaller *Escherichia coli* cells were inadequate to deflect them to Outlet C; therefore they exited the channel through Outlet D still, as shown in FIG. 2C. This resulted in spatial separation of particles/cells mixture at the end of channel. We were able to separate ~$10^6$ particles from ~$10^6$ cells per hour with 1.5 μl/min flow rate. Simply increasing the flow rate can further increase sorting throughput. Current microfluidic sorting schemes use flow rates ranging between ~10 μl/min and ~1 ml/min (Gossett et al. 2010). With such flow rates and $10^7$-$10^8$ cells/ml concentration, maximum sorting throughput of our device in theory can go up to $10^9$ cells per hour.

Figures 4A, 4B, 4C, 4D, 4E, 4F, 4G, 4H, 4I:
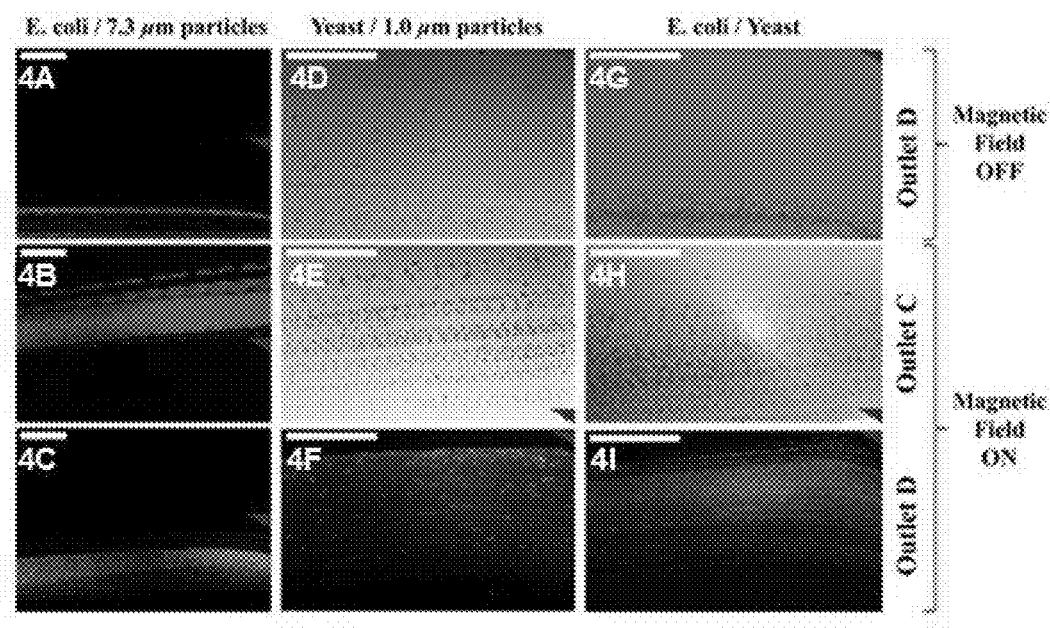
FIGS. 4A-4I illustrate experimental composite micrographs of sorting process.

Secondly, we calibrated the device using a mixture of *Saccharomyces cerevisiae* cells and green fluorescent 1.0 μm particles, which have similar volume as *Escherichia coli* cells. *Saccharomyces cerevisiae* were stained with red nucleic acid stain SYTO17. Both particles and cells again have concentrations of ~$10^7$ counts/ml. Due to weak red fluorescence from SYTO17 in our setup, we chose to use a combination of bright-field and fluorescent modes microscopy to record the sorting process. FIG. 4D shows merged composite micrograph of green fluorescent 1.0 μm particles and bright-field particles/*Saccharomyces cerevisiae* mixture, both of which exited channel through Outlet D when magnetic fields were off. Sorting of this mixture was achieved as soon as magnetic fields were on, as depicted in FIGS. 4E-4F. Cells distribution analysis presented in the following section confirmed a close to 100% sorting efficiency. Sorting throughput was ~$10^6$ cells per hour. Here we demonstrated that combination of bright-field and fluorescent microscopy can successfully circumvent recording issues originating from opaqueness of ferrofluids and weak fluorescence from stained live cells.

Finally, sorting of *Escherichia coli* and *Saccharomyces cerevisiae* cells were carried out in the same device at the same time. *Escherichia coli* cells were stained with green fluorescence while *Saccharomyces cerevisiae* were stained with red fluorescence. Both types of cells were adjusted to ~$10^7$ cells/ml concentration in initial mixture. It is clearly shown in FIG. 4G that all cells exited from the channel through Outlet D when there was no magnetic field. Both bright-field and fluorescent mode micrographs of cells were recorded and merged to form FIG. 4G. *Saccharomyces cerevisiae* cells were successfully sorted from the initial cell mixture with the application of magnetic fields, as demonstrated in FIGS. 4H-4I.

Figures 8A, 8B, 8C, 8D, 8E, 8F, 8G, 8H, 8I, 8J:
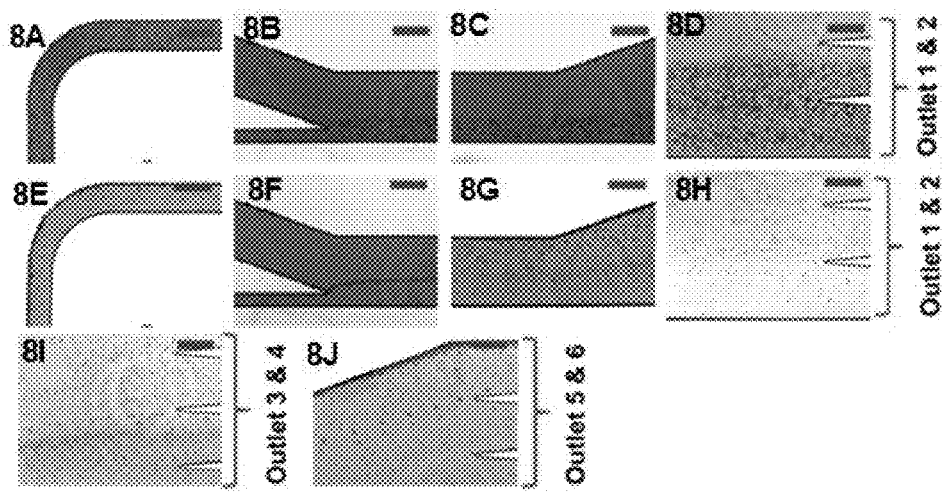
FIGS. 8A-8J illustrate experimental composite micrographs of focusing and sorting process.

In the second embodiment, mouse red blood cell pellet were collected from centrifugation of whole blood. Both red blood cells and Hela cells have concentrations of ~$2\times10^6$ counts/ml. We introduced cells mixture into microfluidic channel Inlet A at a constant flow rate of 8 μl/min. The mixture was hydrodynamically focused into a narrow stream by sheath flow from Inlet B at a flow rate of 14 μl/min. The observation window was located at four different sections, as indicated in FIGS. 8A-8D. When magnetic fields were off, particles and cells were flowing together near sidewall of the channel and exiting through Outlet 1, as shown in composite micrograph of FIG. 8D. When magnetic fields were on, magnetic buoyancy forces deflected particles towards the inlet wall as shown in FIG. 8E, then hydrodynamically focused into a narrow stream as shown in FIG. 8F. HeLa Cells were separated due to the larger size as shown in FIG. 8G and deflected towards outlet 5-6, as shown in FIG. 8J. On the other hand, forces on smaller red blood cells were inadequate; therefore they exited the channel through Outlet 1-4, as shown in FIGS. 8H-8I. This resulted in spatial separation of cells mixture at the end of channel.

FIGS. 11A-11D were superimposed micrographs of 15.5 μm and 5.8 μm particles particles mixture. FIGS. 11E-11H illustrate HeLa cell and 5.8 μm particles particles mixture. FIGS. 11A, 11B, 11E, 11F illustrate micrographs of inlets and outlets before magnetic fields were applied. FIGS. 11C, 11D, 11G, 11H illustrate micrographs of inlets and outlets after magnetic fields were applied.

Figures 10A, 10B, 10C, 10D:
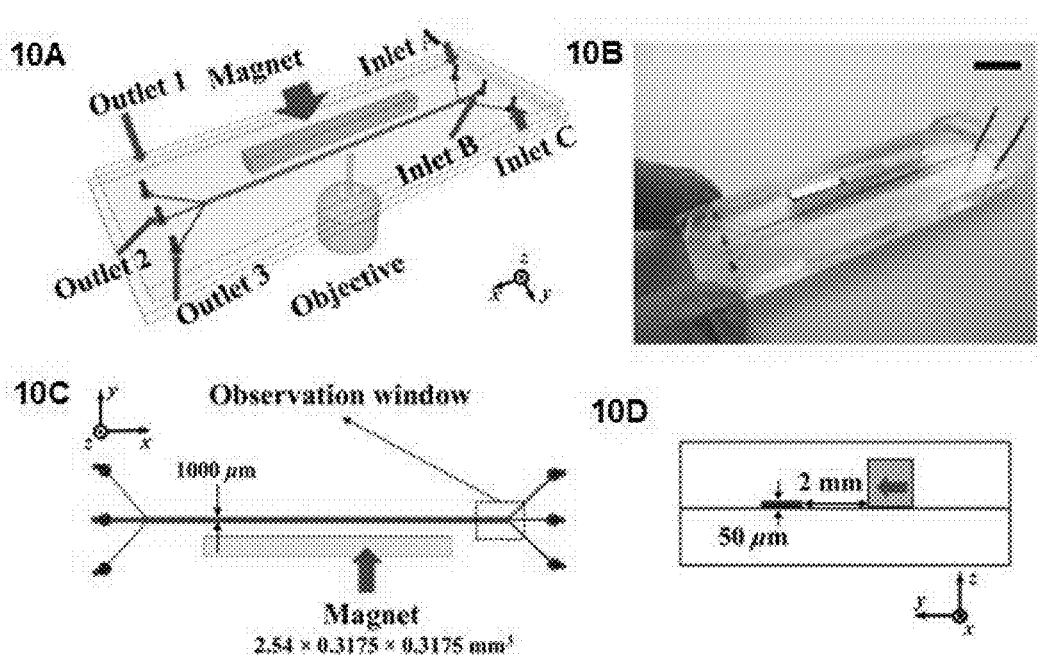
FIG. 10A illustrates a schematic representation of the sorting device with permanent magnets and a microfluidic channel.
FIG. 10B illustrates an image of protype device. Scale bar is 10 mm.
FIG. 10C illustrates a topview of the device and relevant dimensions. The arrows indicate direction of magnets' magnetization.
FIG. 10D illustrates a cross-section of the device.
Figures 11A, 11B, 11C, 11D, 11E, 11F, 11G, 11H:
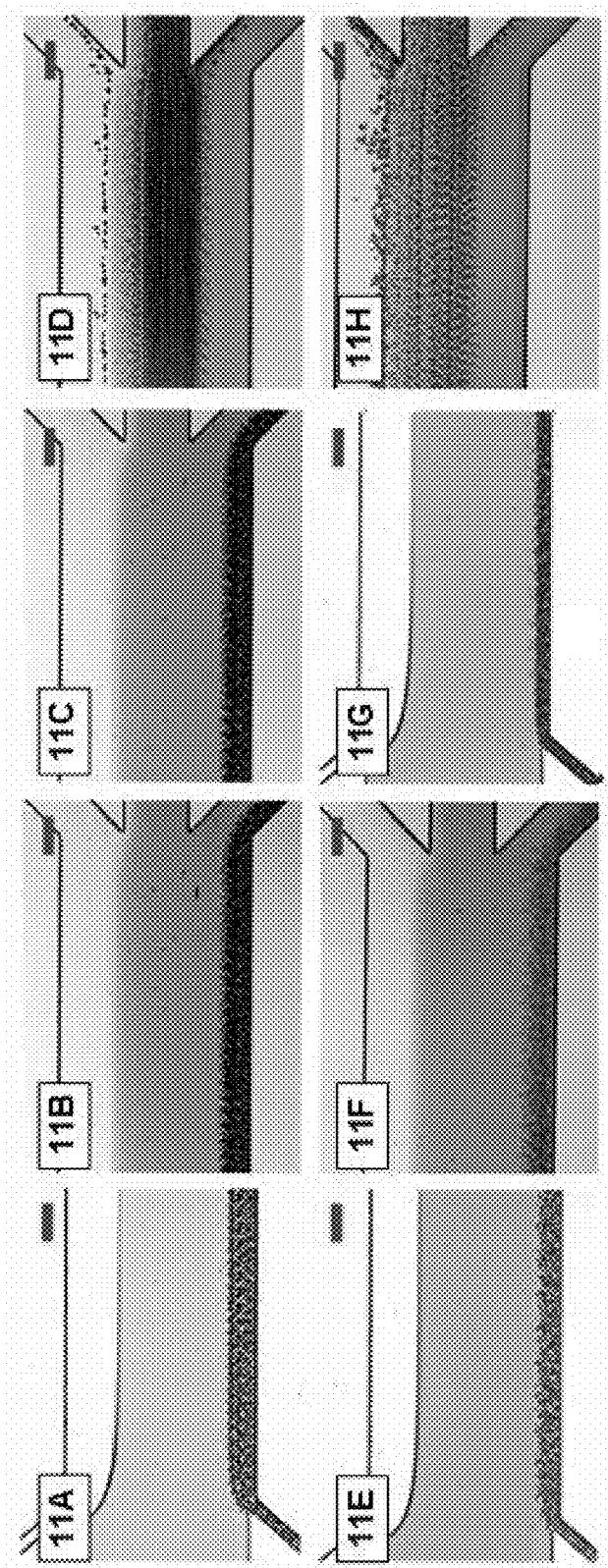
FIGS. 11A-11H illustrates an experimental composite micrographs of sorting process.

In the third embodiment, we demonstrated sorting process using a mixture of 5.8 μm and 15.5 μm polystyrene particles. Both particles and cells have concentrations of ~$2\times10^6$ counts/ml. We introduced microparticles/cells mixture in HBSS or ferrofluids into microfluidic channel Inlet A at a constant flow rate of 1.5 μl/min. The mixture was hydrodynamically focused into a narrow stream by sheath flow from Inlet B at a flow rate of 4 μl/min and a third HBSS flow at a flow rate of 6 μl/min. The observation window was located right before the channel outlets, as indicated in FIG. 10C. When magnetic fields were off, particles and cells were flowing together near sidewall of the channel and exiting through Outlet 1, as shown in composite micrograph of FIG. 11B. When magnetic fields were on, magnetic buoyancy forces deflected particles from their laminar flow paths towards Outlet 3, as shown in FIG. 11D. On the other hand, forces on smaller *Escherichia coli* cells were inadequate to deflect them to Outlet 3; therefore they exited the channel through Outlet 1 and 2, as shown in FIG. 11D. This resulted in spatial separation of particles/cells mixture at the end of channel. Simply increasing the flow rate can further increase sorting throughput. Current microfluidic sorting schemes use flow rates ranging between ~10 μl/min and ~1 ml/min (Gossett et al. 2010). With such flow rates and $10^7$-$10^8$ cells/ml concentration, maximum sorting throughput of our device in theory can go up to $10^9$ cells per hour.

Figures 5A, 5B, 5C, 5D, 5E, 5F, 5G, 5H, 5I, 5J, 5K, 5L:
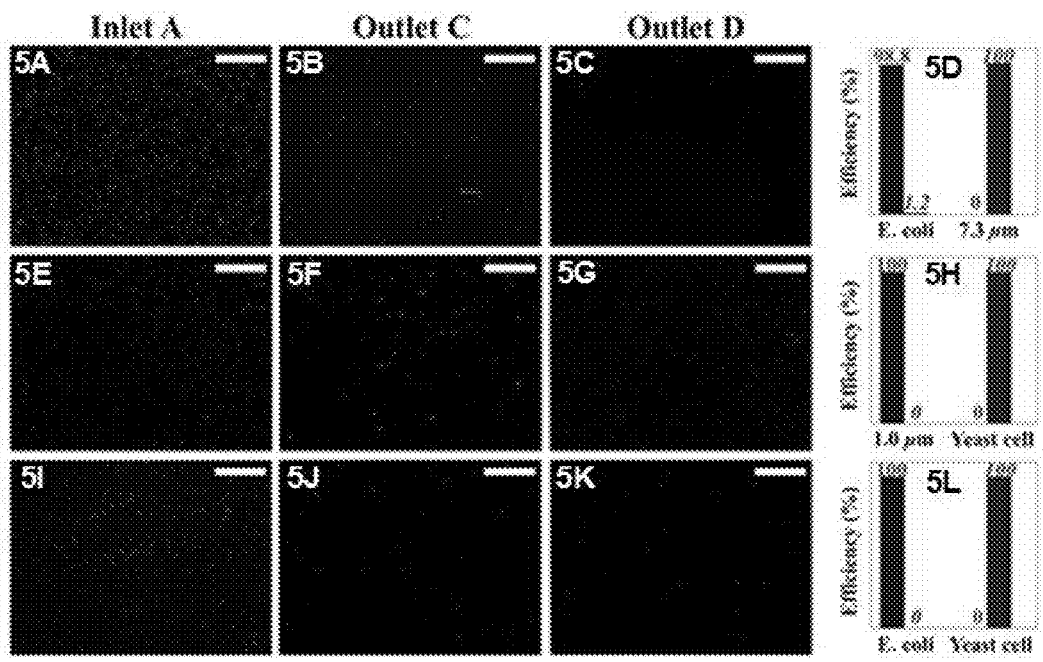
FIGS. 5A-5L illustrate experimental composite micrographs of size distribution analysis, including micrographs of particles/cells mixture collected before sorting at Inlet A and after separation at Outlets C and D, and remaining and separation efficiencies.

Cell Sorting Efficiency:

In order to precisely evaluate sorting efficiency, in the first embodiment, we collected samples from both Outlets C and D and analyzed them for size distributions off chip. We stained cells in distinctive fluorescence and counted them using ImageJ® software. Specifically, in first calibration, *Escherichia coli* cells were green and 7.3 μm particles were red; in second calibration, *Saccharomyces cerevisiae* cells were red and 1.0 μm particles were green; in cells sorting, *Saccharomyces cerevisiae* cells were red and *Escherichia coli* cells were green. Fluorescent mode was chosen for distribution analysis to avoid miscounting of cell types in bright-field micrographs. A magnetic field was applied to push all particles and cells onto a surface of glass slide to increase visibility. We define remaining efficiency as ratio of number of particles or cells exiting from Outlet D after magnetic field application to their initial number before magnetic field application. Similarly, sorting efficiency is defined as the ratio of number of particles or cells exiting from Outlet C after magnetic field application to their initial number before magnetic field application. FIG. 5A shows a representative composite micrograph of *Escherichia coli* cells and 7.3 µm particles collected from Inlet A before sorting. 100% of 7.3 µm particles migrated to Outlet C and 98.8% *Escherichia coli* cells remained in Outlet D, as depicted in FIGS. 5B-5C. Remaining and separation efficiencies for both particles are plotted in FIG. 5D. FIGS. 5E-5H and FIGS. 5I-5L show micrographs and efficiencies for *Saccharomyces cerevisiae* cells/1.0 µm particles mixture sorting and *Saccharomyces cerevisiae* cells/*Escherichia coli* cells mixture sorting, respectively. Both cases have 100% efficiencies. It should be noted that samples collected from Outlets C and D were greatly diluted by ferrofluid sheath flow from Inlet B, rendering much lower particles and cells concentration for distribution analysis. A possible solution to this problem is integration of cell focusing (Zhu et al. 2011a) and sorting steps on one chip.

Figure 9:
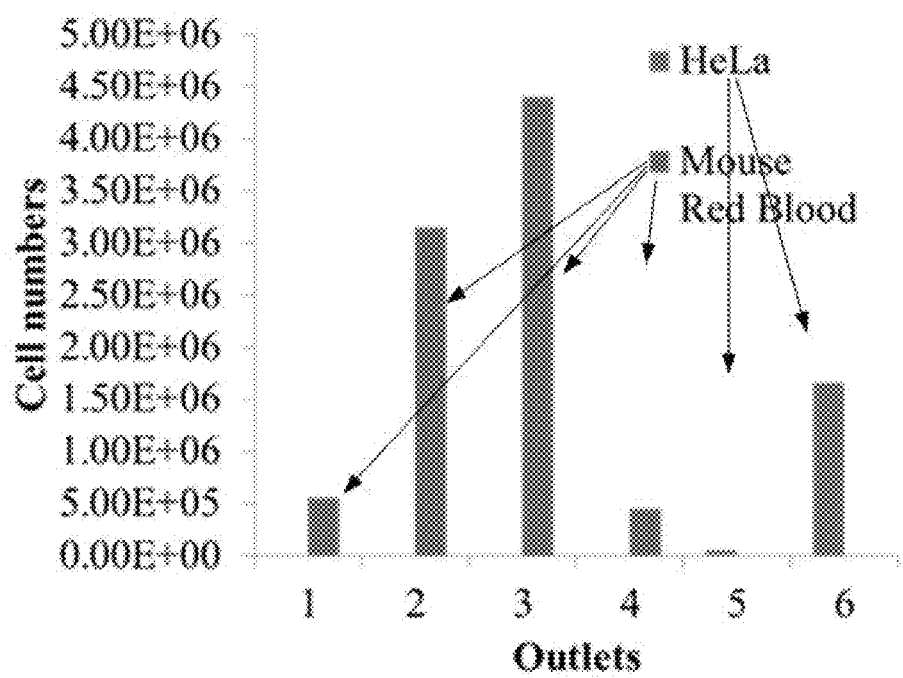
FIG. 9 illustrates the separation efficiency verification of cells distribution in each outlet after separation.

In the second embodiment, we collected samples from multiple outlets and analyzed them for size distributions with a haemocytometer. Phase contrast microscopy was used to visualize cells in bright-field micrographs. FIG. 9 shows the cells distribution in each outlet. 100% of HeLa cells migrated to Outlet 5 and 6 while 100% mouse red blood cells migrated to Outlet 1-4.

In the third embodiment, 100% of 15.5 µm particles migrated to Outlet 3 and 100% 5.8 µm particles migrated to Outlet 1 and 2, as counted with a haemocytometer.

Outlooks of Ferrohydrodynamic Sorting:

Ferrohydrodynamic cell sorting offers the potential for high throughput (~$10^7$ cells/hour in this study and ~$10^9$ cells/hour in theory) and high separation efficiency (~100%) that are comparable to existing microfluidic sorting techniques but without the use of labels. The associated device is inexpensive and simple, only requiring a channel and hand-held permanent magnets. Sorting specificity of this approach is not limited to size difference only; it is also sensitive to cells' shape and deformability (Kose et al. 2009). In adapting it to miniaturized flow cytometry, ferrohydrodynamic manipulation can first focus cells into single cell streams before sorting, eliminating needs for excessive sheath flow and preventing sample dilution (Zhu et al. 2011a). Compared to paramagnetic solution based sorting, ferrofluid offers much higher magnetic susceptibility, eliminating needs for either microfabricated ferromagnetic structures to enhance field gradient or hypertonic concentrations of paramagnetic salts that are not biocompatible for live cell manipulation.

On the other hand, using water-based ferrofluids for cell manipulation is a work in progress. Diagnostic and research applications directed towards simply purifying or isolating cells of interest from complex mixtures such as blood and exfoliated cytology specimens are exciting. For instance, blood cells obscure the detection of the larger but rare abnormal cervical cells from Pap test specimens and metastatic epithelial tumor cells circulating in blood (Moriarty et al. 2009; Yu et al. 2011). Misinterpreted cervical cytology ranks third among causes of medical negligence claims against pathologist (Frable 2007). A simple, low-cost tumor cell enrichment platform would benefit cancer screening. However, two issues, cell visibility and biocompatibility of mammalian cells in ferrofluids, limit applications of ferrohydrodynamic manipulation. Ferrofluids are opaque due to light diffraction from their high concentration of magnetic nanoparticles. Fluorescent cells need to be close to channel surface for microscopic recording. In order to address this issue, ferrofluids with low solid content, as well as shallow microfluidic channel, are favored for cell manipulation. In addition, magnetic fields can be used to push cells onto channel surface, increasing visibility of cells in fluorescent mode. In this study, we used a combination of both bright-field and fluorescent modes microscopy to circumvent the opaqueness issue. Cells were readily visible in a shallow channel in bright-field micrographs. Another potential issue is biocompatibility of ferrofluids. Our next step is to extend this methodology to mammalian cells, particularly human specimens such as blood and other bodily fluids, exfoliated musical cells, and tumor aspirates. The requirements of mammalian cells may differ from *Escherichia coli* and *Saccharomyces cerevisiae*. For cell manipulation, materials, pH value, and surfactants of ferrofluids need to be rendered biocompatible, at the same time the overall colloidal system of ferrofluids must be maintained. Typically, nanoparticles within ferrofluids for cell applications are made of magnetite (Pankhurst et al. 2003). pH value of ferrofluids needs to be compatible with cell culture and maintained at 7.4. Salt concentration, tonicity, and surfactant must be carefully chosen close to physiological conditions to reduce cell death. Although these are stringent requirements, progress has been made towards synthesizing biocompatible ferrofluids. For example, Koser's group used citrate to stabilize cobalt-ferrite nanoparticles for live red blood cell and *Escherichia coli* cell sorting (Kose et al. 2009). Yellen's group used Bovine Serum Albumin (BSA) to stabilize magnetite nanoparticles for human umbilical vein endothelial cells manipulation (Krebs Melissa et al. 2009). Viability tests from both studies have shown cells were able to retain their viability for up to several hours in ferrofluids. In our study, a commercially available pH ~7 magnetite ferrofluid was able to sustain viability of both *Escherichia coli* and *Saccharomyces cerevisiae* cells for at least 2 hours.

CONCLUSION

In conclusion, we have developed a label-free and continuous-flow ferrohydrodynamic cell sorting device and applied it in separating *Escherichia coli* and *Saccharomyces cerevisiae* cells. A commercial magnetite ferrofluid was used to separate particle and cell mixtures. A lab customized ferrofluid was used to separate mammalian cells. Construction of our device is simple and low-cost; we choose to use permanent magnets instead of integrated electrodes to eliminate complex microfabrication process and auxiliary power supply. Current sorting throughput is $10^7$ cells/hour, and sorting efficiency is close to 100%. We envision this device can achieve up to two orders higher throughput while still maintaining current sorting efficiency.

REFERENCES, EACH OF WHICH IS INCORPORATED HEREIN BY REFERENCE

Adams A A, Okagbare P I, Feng J, Hupert M L, Patterson D, Gottert J, McCarley R L, Nikitopoulos D, Murphy M C, Soper S A (2008) Highly efficient circulating tumor cell isolation from whole blood and label-free enumeration using polymer-based microfluidics with an integrated conductivity sensor. J Am Chem Soc 130 (27):8633-8641. doi:Doi 10.1021/Ja8015022

Beyor N, Seo T S, Liu P, Mathies R A (2008) Immunomagnetic bead-based cell concentration microdevice for dilute pathogen detection. Biomed Microdevices 10 (6):909-917. doi:Doi 10.1007/S10544-008-9206-3

Bonner W A, Sweet R G, Hulett H R, Herzenbe. La (1972) Fluorescence Activated Cell Sorting. Review of Scientific Instruments 43 (3):404-409.

Brody J P, Yager P, Goldstein R E, Austin R H (1996) Biotechnology at low Reynolds numbers. Biophys J 71 (6):3430-3441.

Davis J A, Inglis D W, Morton K J, Lawrence D A, Huang L R, Chou S Y, Sturm J C, Austin R H (2006) Deterministic hydrodynamics: Taking blood apart. P Natl Acad Sci USA 103 (40):14779-14784. doi:Doi 10.1073/Pnas.0605967103

Dharmasiri U, Witek M A, Adams A A, Osiri J K, Hupert M L, Bianchi T S, Roelke D L, Soper S A (2010) Enrichment and Detection of *Escherichia coli* O157:H7 from Water Samples Using an Antibody Modified Microfluidic Chip. Analytical Chemistry 82 (7):2844-2849. doi:Doi 10.1021/Ac100323k Di Carlo D (2009) Inertial microfluidics. Lab on a Chip 9 (21):3038-3046. doi:Doi 10.1039/B912547g Frable W J (2007) Error reduction and risk management in cytopathology. Semin Diagn Pathol 24 (2):77-88.

Furlani E P, Sahoo Y (2006) Analytical model for the magnetic field and force in a magnetophoretic microsystem. J Phys D Appl Phys 39 (9):1724-1732. doi:Doi 10.1088/0022-3727/39/9/003

Gijs M A M, Lacharme F, Lehmann U (2010) Microfluidic Applications of Magnetic Particles for Biological Analysis and Catalysis. Chem Rev 110 (3):1518-1563.

Gossett D R, Weaver W M, Mach A J, Hur S C, Tse H T K, Lee W, Amini H, Di Carlo D (2010) Label-free cell separation and sorting in microfluidic systems. Analytical and Bioanalytical Chemistry 397 (8):3249-3267.

Hafeli U, Schutt W, Teller J, Zborowski M (1997) Scientific and clinical applications of magnetic carriers. Springer, New York.

Hatch A, Kamholz A E, Holman G, Yager P, Bohringer K F (2001) A ferrofluidic magnetic micropump. Microelectromechanical Systems, Journal of 10 (2):215-221.

Hoshino K, Huang Y Y, Lane N, Huebschman M, Uhr J W, Frenkel E P, Zhang X J (2011) Microchip-based immunomagnetic detection of circulating tumor cells. Lab on a Chip 11 (20):3449-3457. doi:Doi 10.1039/C1lc20270g Huang L R, Cox E C, Austin R H, Sturm J C (2004) Continuous particle separation through deterministic lateral displacement. Science 304 (5673):987-990. doi: 10.1126/science.1094567 304/5673/987

Jorgensen P, Nishikawa J L, Breitkreutz B J, Tyers M (2002) Systematic identification of pathways that couple cell growth and division in yeast. Science 297 (5580):395-400. doi:Doi 10.1126/Science. 1070850

Kaya T, Koser H (2009) Characterization of Hydrodynamic Surface Interactions of *Escherichia coli* Cell Bodies in Shear Flow. Physical Review Letters 103 (13):138103. doi:Artn 138103 Doi 10.1103/Physrevlett.103.138103

Kose A R, Fischer B, Mao L, Koser H (2009) Label-free cellular manipulation and sorting via biocompatible ferrofluids. P Natl Acad Sci USA 106 (51):21478-21483. doi:Doi 10.1073/Pnas.0912138106

Kose A R, Koser H (2012) Ferrofluid mediated nanocytometry. Lab on a Chip 12 (1):190-196. doi:Doi 10.1039/C1lc20864k Krebs Melissa D, Erb Randall M, Yellen Benjamin B, Samanta B, Bajaj A, Rotello Vincent M, Alsberg E (2009) Formation of ordered cellular structures in suspension via label-free negative magnetophoresis. Nano Lett 9 (5):1812-1817.

Laurell T, Petersson F, Nilsson A (2007) Chip integrated strategies for acoustic separation and manipulation of cells and particles. Chem Soc Rev 36 (3):492-506. doi: Doi 10.1039/B601326k Lee H, Purdon A M, Chu V, Westervelt R M (2004) Controlled assembly of magnetic nanoparticles from magnetotactic bacteria using microelectromagnets arrays. Nano letters 4 (5):995-998. doi:Doi 10.1021/Nl049562x Lenshof A, Laurell T (2010) Continuous separation of cells and particles in microfluidic systems. Chem Soc Rev 39 (3):1203-1217. doi:Doi 10.1039/B915999c Liang L T, Zhu J J, Xuan X C (2011) Three-dimensional diamagnetic particle deflection in ferrofluid microchannel flows. Biomicrofluidics 5 (3):034110. doi:Artn 034110 Doi 10.1063/1.3618737

Liu C X, Stakenborg T, Peeters S, Lagae L (2009) Cell manipulation with magnetic particles toward microfluidic cytometry. J Appl Phys 105 (10):102014. doi:Artn 102014 Doi 10.1063/1.3116091

Liu R H, Yang J N, Lenigk R, Bonanno J, Grodzinski P (2004) Self-contained, fully integrated biochip for sample preparation, polymerase chain reaction amplification, and DNA microarray detection. Analytical Chemistry 76 (7):1824-1831. doi:Doi 10.1021/Ac0353029

Love L J, Jansen J F, McKnight T E, Roh Y, Phelps T J (2004) A magnetocaloric pump for microfluidic applications. Ieee T Nanobiosci 3 (2):101-110. doi:Doi 10.1109/Tnb.2004.828265

Mao L, Koser H Overcoming the Diffusion Barrier: Ultra-Fast Micro-Scale Mixing Via Ferrofluids. In: 14th International Conference on Solid-State Sensors, Actuators and Microsystems, Lyon, France, 2007. pp 1829-1832.

Mao L D, Elborai S, He X W, Zahn M, Koser H (2011) Direct observation of closed-loop ferrohydrodynamic pumping under traveling magnetic fields. Phys Rev B 84 (10):104431. doi:Artn 104431 Doi 10.1103/Physrevb.84.104431

Mao L D, Koser H (2006) Towards ferrofluidics for mu-TAS and lab on-a-chip applications. Nanotechnology 17 (4):S34-S47. doi:Doi 10.1088/0957-4484/17/4/007

Mihajlovic G, Aledealat K, Xiong P, Von Molnar S, Field M, Sullivan G J (2007) Magnetic characterization of a single superparamagnetic bead by phase-sensitive micro-Hall magnetometry. Applied Physics Letters 91 (17):172518. doi:Artn 172518 Doi 10.1063/1.2802732

Miller M M, Sheehan P E, Edelstein R L, Tamanaha C R, Zhong L, Bounnak S, Whitman L J, Colton R J (2001) A DNA array sensor utilizing magnetic microbeads and magnetoelectronic detection. J Magn Magn Mater 225 (1-2):138-144.

Miltenyi S, Muller W, Weichel W, Radbruch A (1990) High-Gradient Magnetic Cell-Separation with Macs. Cytometry 11 (2):231-238.

Mirica K A, Shevkoplyas S S, Phillips S T, Gupta M, Whitesides G M (2009) Measuring Densities of Solids and Liquids Using Magnetic Levitation: Fundamentals. Journal of the American Chemical Society 131 (29):10049-10058. doi:Doi 10.1021/Ja900920s Moriarty A T, Clayton A C, Zaleski S, Henry M R, Schwartz M R, Eversole G M, Tench W D, Fatheree L A, Souers R J, Wilbur D C (2009) Unsatisfactory reporting rates: 2006 practices of participants in the college of american pathologists interlaboratory comparison program in gynecologic cytology. Arch Pathol Lab Med 133 (12):1912-1916. doi:2008-0793-CPR1 [pii] 10.1043/1543-2165-133.12.1912

Nagrath S, Sequist L V, Maheswaran S, Bell D W, Irimia D, Ulkus L, Smith M R, Kwak E L, Digumarthy S, Muzikansky A, Ryan P, Balis U J, Tompkins R G, Haber D A, Toner M (2007) Isolation of rare circulating tumour cells in cancer patients by microchip technology. Nature 450 (7173):1235-1239. doi:nature06385 [pii] 10.1038/nature06385

Nguyen N T (2012) Micro-magnetofluidics: interactions between magnetism and fluid flow on the microscale. Microfluidics and Nanofluidics 12 (1-4):1-16. doi:Doi 10.1007/S10404-011-0903-5

Nguyen N T, Ng K M, Huang X Y (2006) Manipulation of ferrofluid droplets using planar coils. Applied Physics Letters 89 (5):052509. doi:Artn 052509 Doi 10.1063/1.2335403

Odenbach S, Editor (2002) Ferrofluids: Magnetically Controllable Fluids and Their Applications. Springer, London.

Pamme N (2006) Magnetism and microfluidics. Lab Chip 6 (1):24-38. doi:Doi 10.1039/B513005k Pamme N (2007) Continuous flow separations in microfluidic devices. Lab Chip 7 (12):1644-1659. doi:Doi 10.1039/B712784g Pankhurst Q A, Connolly J, Jones S K, Dobson J (2003) Applications of magnetic nanoparticles in biomedicine. Journal of Physics D: Applied Physics (13):R167-R181.

Peyman S A, Iwan E Y, Margarson O, Iles A, Pamme N (2009) Diamagnetic repulsion-A versatile tool for label-free particle handling in microfluidic devices. J Chromatogr A 1216 (52):9055-9062. doi:Doi 10.1016/J.Chroma.2009.06.039

Rife J C, Miller M M, Sheehan P E, Tamanaha C R, Tondra M, Whitman L J (2003) Design and performance of GMR sensors for the detection of magnetic microbeads in biosensors. Sensors and Actuators a-Physical 107 (3):209-218. doi:Doi 10.1016/S0924-4247(03)00380-7

Rodriguez-Villarreal A I, Tarn M D, Madden L A, Lutz J B, Greenman J, Samitier J, Pamme N (2011) Flow focussing of particles and cells based on their intrinsic properties using a simple diamagnetic repulsion setup. Lab on a Chip 11 (7):1240-1248. doi:Doi 10.1039/C0lc00464b Rosensweig R E (1985) Ferrohydrodynamics. Cambridge University Press, Cambridge.

Shen F, Hwang H, Hahn Y K, Park J-K (2012) Label-Free Cell Separation Using a Tunable Magnetophoretic Repulsion Force. Analytical Chemistry. doi:10.1021/ac201505j Shevkoplyas S S, Siegel A C, Westervelt R M, Prentiss M G, Whitesides G M (2007) The force acting on a superparamagnetic bead due to an applied magnetic field. Lab Chip 7 (10):1294-1302. doi:Doi 10.1039/B705045c Shi J J, Huang H, Stratton Z, Huang Y P, Huang T J (2009) Continuous particle separation in a microfluidic channel via standing surface acoustic waves (SSAW). Lab on a Chip 9 (23):3354-3359. doi:Doi 10.1039/B915113c Sun Y, Kwok Y C, Nguyen N T (2007) A circular ferrofluid driven microchip for rapid polymerase chain reaction. Lab on a Chip 7 (8):1012-1017. doi:Doi 10.1039/B700575j Sun Y, Nguyen N T, Kwok Y C (2008) High-throughput polymerase chain reaction in parallel circular loops using magnetic actuation. Analytical Chemistry 80 (15):6127-6130. doi:Doi 10.1021/Ac800787g Toner M, Irimia D (2005) Blood-on-a-chip. Annu Rev Biomed Eng 7:77-103. doi:Doi 10.1146/Annurev.Bioeng.7.011205.135108

Tsutsui H, Ho C M (2009) Cell separation by non-inertial force fields in microfluidic systems. Mechanics Research Communications 36 (1):92-103. doi:Doi 10.1016/J.Mechrescom.2008.08.006

Voldman J (2006) Electrical forces for microscale cell manipulation. Annu Rev Biomed Eng 8:425-454. doi:Doi 10.1146/Annurev.Bioeng.8.061505.095739

Wang Z C, Zhe J A (2011) Recent advances in particle and droplet manipulation for lab-on-a-chip devices based on surface acoustic waves. Lab on a Chip 11 (7):1280-1285. doi:Doi 10.1039/C0lc00527d Winkleman A, Perez-Castillejos R, Gudiksen K L, Phillips S T, Prentiss M, Whitesides G M (2007) Density-based diamagnetic separation: Devices for detecting binding events and for collecting unlabeled diamagnetic particles in paramagnetic solutions. Analytical Chemistry 79 (17):6542-6550. doi:Doi 10.1021/Ac070500b Yamada M, Nakashima M, Seki M (2004) Pinched flow fractionation: Continuous size separation of particles utilizing a laminar flow profile in a pinched microchannel. Analytical Chemistry 76 (18):5465-5471. doi:Doi 10.1021/Ac049863r Yellen B B, Hovorka O, Friedman G (2005) Arranging matter by magnetic nanoparticle assemblers. P Natl Acad Sci USA 102 (25):8860-8864. doi:Doi 10.1073/Pnas.0500409102

Yu M, Stott S, Toner M, Maheswaran S, Haber D A (2011) Circulating tumor cells: approaches to isolation and characterization. J Cell Biol 192 (3):373-382. doi:jcb.201010021 [pii] 10.1083/jcb.201010021

Yung C W, Fiering J, Mueller A J, Ingber D E (2009) Micromagnetic-microfluidic blood cleansing device. Lab Chip 9 (9):1171-1177. doi:Doi 10.1039/B816986a Zborowski M, Ostera G R, Moore L R, Milliron S, Chalmers J J, Schechter A N (2003) Red blood cell magnetophoresis. Biophys J 84 (4):2638-2645.

Zhang K, Liang Q L, Ai X N, Hu P, Wang Y M, Luo G A (2011a) Comprehensive Two-Dimensional Manipulations of Picoliter Microfluidic Droplets Sampled from Nanoliter Samples. Analytical Chemistry 83 (20):8029-8034. doi:Doi 10.1021/Ac2017458

Zhang K, Liang Q L, Ai X N, Hu P, Wang Y M, Luo G A (2011b) On-demand microfluidic droplet manipulation using hydrophobic ferrofluid as a continuous-phase. Lab on a Chip 11 (7):1271-1275. doi:Doi 10.1039/C0lc00484g Zhu J J, Liang L T, Xuan X C (2012) On-chip manipulation of nonmagnetic particles in paramagnetic solutions using embedded permanent magnets. Microfluidics and Nanofluidics 12 (1-4):65-73. doi:Doi 10.1007/S10404-011-0849-7

Zhu T T, Cheng R, Mao L D (2011a) Focusing microparticles in a microfluidic channel with ferrofluids. Microfluidics and Nanofluidics 11 (6):695-701. doi:Doi 10.1007/S10404-011-0835-0

Zhu T T, Lichlyter D J, Haidekker M A, Mao L D (2011b) Analytical model of microfluidic transport of non-magnetic particles in ferrofluids under the influence of a permanent magnet. Microfluidics and Nanofluidics 10 (6):1233-1245. doi:Doi 10.1007/S10404-010-0754-5

Zhu T T, Marrero F, Mao L D (2010) Continuous separation of non-magnetic particles inside ferrofluids. Microfluidics and Nanofluidics 9 (4-5):1003-1009

Example 2

Currently, we are developing a type of water based ferrofluids that can facilitate cervical cancer cells sorting. To maintain the nonmagnetic properties of cancer cells, cellular uptake of magnetic nanoparticles should be minimized. Interaction between cells and magnetic nanoparticles were known to be caused by endocytosis and physical attraction (Verma and Stellacci 2010), which are dictated by the surface properties. Polyethyene glycol and phosphorylcholine based copolymer was chosen as the surfactant to stabilize magnetite ($Fe_3O_4$) nanoparticles for their excellent biocompatibility (Yuan, Armes et al. 2006; Józefczak, Hornowski et al. 2009). Biomemetic phospholipid polar group were also proven to inhibit non-selective cellular uptake of nanoparticles (Ishihara and Takai 2009). Copolymer structure provides more flexibility with anchoring group and functional group, however, multiple groups can also easily interact with several nanoparticles leading to flocculation (Boyer, Whittaker et al. 2010). Once the colloidal stable ferrofluids are developed, cancer cells viability and cellular uptake of nanoparticles will be measured (Samanta, Yan et al. 2008). Positive results will enable the application of ferrofluids combing microfluidic platform as the cancer cells sorter.

Boyer, C., M. R. Whittaker, et al. (2010). "The design and utility of polymer-stabilized iron-oxide nanoparticles for nanomedicine applications." *NPG Asia Mater* 2: 23-30.

Ishihara, K. and M. Takai (2009). "Bioinspired interface for nanobiodevices based on phospholipid polymer chemistry." *Journal of The Royal Society Interface* 6(Suppl 3): S279-S291.

Józefczak, A., T. Hornowski, et al. (2009). "Effect of poly (ethylene glycol) coating on the magnetic and thermal properties of biocompatible magnetic liquids." *Journal of Magnetism and Magnetic Materials* 321(10): 1505-1508.

Samanta, B., H. Yan, et al. (2008). "Protein-passivated Fe3O4 nanoparticles: low toxicity and rapid heating for thermal therapy." *Journal of Materials Chemistry* 18(11): 1204-1208. Verma, A. and F. Stellacci (2010). "Effect of Surface Properties on Nanoparticle—Cell Interactions." *Small* 6(1): 12-21.

Yuan, J. J., S. P. Armes, et al. (2006). "Synthesis of Biocompatible Poly[2-(methacryloyloxy)ethyl phosphorylcholine]-Coated Magnetite Nanoparticles." *Langmuir* 22(26): 10989-10993.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to the measurement technique and the type of numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

We claim:

1. A method for separating particles from a liquid comprising a magnetic fluid and at least two types of particles having different volumes, the method comprising:
    flowing the liquid down a channel having two or more outlets in fluidic communication with the channel;
    exposing the magnetic fluid to a non-uniform magnetic force to control the non-uniform magnetic force exerted on the particles and magnetic buoyancy force experienced by the particles; and
    separating the at least two types of particles into different outlets of the two or more outlets based on the magnetic buoyancy force and the volume of the particles;
    wherein the particles are cells.

2. The method of claim 1, wherein the at least two types of particles are separated at a rate of about $10^6$ particles per hour to about $10^9$ particles per hour.

3. The method of claim 1, wherein the cells are selected from the group consisting of bacterial cells, yeast cells, blood cells, cancer cells, neural cells, and sperm cells.

4. The method of claim 1, wherein each of the cells has a volume of 5 $\mu m^3$ to 3000 $\mu m^3$.

5. The method of claim 1, wherein the particles are separated based upon a difference in the magnetic buoyancy force experienced due to the different volumes of the particles.

6. The method of claim 1, wherein the channel has two or more fluid inlets in fluidic communication with the channel, wherein the method further comprises flowing the at least two types of particles through a first fluid inlet and flowing the magnetic fluid through a second fluid inlet to form the liquid.

7. The method of claim 6, wherein the first fluid inlet includes at least two turns prior to the channel.

8. The method of claim 1, wherein the channel includes three or more outlets for separating particles based upon the different volumes.

9. The method of claim 1, wherein the channel has a tapered diameter along a portion of the length of the channel.

10. The method of claim 1, wherein a magnet disposed on one side of the channel generates the non-uniform magnetic force.

11. The method of claim 10, wherein the magnet is a permanent magnet.

12. The method of claim 1, wherein the magnetic fluid is a colloidal mixture of nano-size magnetic particles covered by a surfactant.

13. The method of claim 12, wherein the nano-size magnetic particles have a diameter of 5 nm to 10 nm.

14. The method of claim 1, wherein the magnetic fluid is a ferrofluid, a paramagnetic solution, or a combination thereof.

* * * * *